United States Patent [19]

Bohnenkamp

[11] Patent Number: 5,221,958
[45] Date of Patent: Jun. 22, 1993

[54] REFLECTION FLUOROMETER

[76] Inventor: Wolfram Bohnenkamp, Thingoltstr. 24, 7750 Konstanz, Fed. Rep. of Germany

[21] Appl. No.: 781,154
[22] PCT Filed: Apr. 28, 1990
[86] PCT No.: PCT/EP90/00688
 § 371 Date: Dec. 31, 1991
 § 102(e) Date: Dec. 31, 1991
[87] PCT Pub. No.: WO90/13808
 PCT Pub. Date: Nov. 15, 1990

[30] Foreign Application Priority Data

May 1, 1989 [CH] Switzerland ............... 1621/89
Dec. 29, 1989 [DE] Fed. Rep. of Germany ....... 3943252
Feb. 20, 1990 [DE] Fed. Rep. of Germany ....... 4005245

[51] Int. Cl.⁵ .................. G01J 3/443; G01N 21/64
[52] U.S. Cl. .................. 356/318; 250/458.1; 356/417
[58] Field of Search ............ 356/317, 318, 417; 250/458.1, 459.1, 461.1, 461.2; 385/12

[56] References Cited

U.S. PATENT DOCUMENTS 4,708,941 11/1987 Giuliani ................ 385/12
4,867,559 9/1989 Bach .................... 356/417
4,880,752 11/1989 Keck et al. .............. 356/317

Primary Examiner—F. L. Evans
Attorney, Agent, or Firm—Evenson, McKeown, Edwards & Lenahan

[57] ABSTRACT

A reflection fluorometer has a cylindrical measuring optical waveguide with a capillary-like structure which permits a beam of pulsed light in the form of a conical envelope to be directed onto a front face of the measuring optical waveguide. The reflection fluorometer comprises a device for timed measurement of the emission light which emerges essentially radially from the measuring optical waveguide.

9 Claims, 3 Drawing Sheets

REFLECTION FLUOROMETER

TECHNICAL FIELD

The present invention relates to a reflection fluorometer having a cylindrical measuring fiber-optical waveguide.

When a light wave impinges on the interface of two media with different refractive indices at a certain angle, it can be totally reflected if the angle of incidence $\Theta$ is larger than the critical angle $\Theta_c$. This angle is calculated from the equation $$\Theta_c = \sin^{-1}(n2/n1),$$

wherein n1 and n2 are the refractive indices of the different media, and $n2 < n1$. At the site of the reflection, a wave is generated in the optically thinner medium which builds up an energy field close to the interface. The use of this energy field (evanescent wave) for optical analyses has been known for a long time: the absorption effects in the case of total reflection on the interface of two optical media are even the classical method for the proof of these energy fields (C. Schaefer, *Zeitschrift fur Physik* (Journal for Physics), 75 [1932] 687–694).

The use of this energy field for analytical measurements has several advantages in comparison to conventional excitation. A stronger energy coupling may occur within the thin film which, as a rule, leads to a reduction of the background signal and therefore to a better signal/noise ratio.

STATE OF THE ART

Devices for measuring fluorescence, which is excited by total reflection, use fibers, cells or capillaries (EP-A 0202021, EP-A 0205236, EP-A 0245206, EP-A 0209489, EP-A 0239382, EP-A 0075353, DE-A 3605518, U.S.-A Pat. No. 4654532 and U.S.-A Pat. No. 4716121). In the DE-A 3605518, a tube-shaped measuring an optical waveguide for a fluorometer is described. The ends of the measuring fiber-optical waveguide are constructed as spherical or conical windows for the enlargement of the entrance cross-section for the exciting light. For the observation of fluorescence radiation, it is provided that the light is examined which emerges essentially perpendicularly to the axis of the measuring fiber-optical waveguide. For this purpose, for example, the axis of the measuring fiber-optical waveguide is imaged on the entrance slit of the fluorescence spectrometer.

From E. Reichstein, et al., *Anal. Chem.* 60 [1988] 1069-1074, it is known to measure the fluorescence, excited by pulsed laser light, of the fluorescence-marked antibodies fixed in the recesses of a microtitration plate in a time window which is adapted to the relatively long die-away time of the fluorescence of the marker and the rapidly dying-away background fluorescence of the test solution.

DESCRIPTION OF THE INVENTION

It is the task of the present invention to improve the reflection fluorometers having a cylindrical measuring fiber-optical waveguide according to the state of the art with respect to the sensitivity, the signal/noise ratio, the required test volume and the obtainable quantity and quality of information. According to the invention, this task is achieved by the objects defined in the patent claims.

The object of the invention is a reflection fluorometer having a cylindrical measuring fiber-optical waveguide characterized by a capillary-shaped measuring fiber-optical waveguide, a conical-envelope-shaped beaming of pulsed light onto a front face of the measuring fiber-optical waveguide, and a device for the time-resolved measurement of the emission light which emerges essentially radially from the measuring fiber-optical waveguide.

A preferred reflection fluorometer is distinguished by a device for wavelength-resolved measurements.

Furthermore, a reflection fluorometer is preferred in which the measuring fiber-optical waveguide has a mirror on the end which is opposite the beaming-in of the light.

A particularly preferred reflection fluorometer has an auxiliary sensor for the measuring of a part of the reflected light and/or of the emission light for the compensation and correction of the measured values.

Another embodiment is distinguished by the fact that the measuring fiber-optical waveguide is situated on a focal line of a reflector which has an elliptic and/or paraboloidal cross-section. The reflector is preferably followed by a focus adapter.

For introducing the light into the fiber-optical waveguide, a lens system is preferably used according to the invention which produces a beaming-in of light in the shape of a conical envelope. A beaming-in of light in the shape of a conical envelope is to be a guiding of light which is bounded by two concentric cone surfaces with a common peak as the focal point. The area of the angle of incidence $\Theta_{i\,min} - \Theta_{i\,max}$ is selected as a function of the refractive index of the used fiber-optical waveguide. The angle area should be as large as possible so that the total reflection is distributed as uniformly as possible over the interfaces of the fiber-optical waveguide. The largest selected angle of beam of the conical envelope of the light $\Theta_{i\,max}$ should be as large as possible so that as many total reflections as possible are achieved along the length of the fiber-optical waveguide. However, it may only be so large that the reflection angles in the interior of the fiber-optical waveguide are still above the critical angle $\Theta_c$. As a result, the ratio between the beamed-in amount of light and the number of total reflections in the measuring fiber-optical waveguide is reduced which results in an improved signal/noise ratio.

A similar beam guiding can be achieved by means of several conventional fiber-optical waveguides which are correspondingly mounted into a conical holding device.

However, the conical-envelope-shaped beaming-in of light may also be achieved by means of a rotationally symmetrical mirror arrangement. The advantage of such a device is the higher light yield of the exciting light source.

Lasers, which are customary for these purposes, may be used as the light sources. The excitation of the fluorescence takes place by the pulsed beaming-in of the excitation light. The length of the beamed-in light pulses may be varied within wide ranges. Expediently, a range of the pulse length of 0.1–10 ns (nanoseconds) may be used. The pulse frequency amounts to 0.1 Hz–1 GHz. If time-dependent as well as wavelength-dependent measurements are carried out, it is possible to detect several elements to be analyzed in one measuring device almost simultaneously. So-called inner standards may also be entered for the purpose of a measured-value compensation or measured-value correction. As a result, adjusting defects of the capillaries or fluctuations of the laser power, etc. may also be recognized. This makes it possible to document the performance and reliability of the measuring device or of each individual measurement. Diagnostic information can therefore be established together with a data-supported or computer-supported processing.

By means of a mirror of the measuring fiber-optical waveguide on the end which is opposite the beaming-in of the light, the optical path length can be doubled which achieves a better utilization of the light. The expert is familiar with these vapor deposition techniques.

If desired, a small amount of the emerging excitation light may be utilized for absorption or control and correction measurements in order to mathematically or mechanically compensate errors caused, for example, by a fluctuating intensity of the excitation light, non-uniformities of the fiber-optical waveguide or insufficient adjusting. For this purpose, a portion of the light emerging at the front face is directed to an auxiliary sensor or the measuring sensor.

Capillary fiber-optical waveguides are used because, in this case, the ratio of the volume to the inner surface is favorable. For examinations with very diluted solutions, it is useful to keep the ratio of the inner surface to the test volume as large as possible. This increases the sensitivity of the measurement and shortens the reaction times for adsorption processes or bonding reactions which may take place on the inner surface.

For example, a capillary of a length of 100 mm and an inside diameter of 0.56 mm has a volume of 25 $\mu$l and inner surface of 1.77 cm$^2$. In comparison, a recess in a microtitration plate has a volume of approximately 220 $\mu$l and a surface of 1.65 cm$^2$.

In order to increase the entrance cross-section, the front face of the measuring fiber-optical waveguide may have a conically tapering design on the side of the light entrance.

If desired, the inner surface may be activated, for example, by the fixing of antibodies which are specific for the elements to be analyzed. The fixing of the reagents, such as antibodies, which are required for the determination of the elements to be analyzed, on the inner surface of the measuring fiber-optical waveguide takes place according to methods that are known per se.

The fluorescence light emitted by the measuring fiber-optical waveguide may be measured by means of a conventional measuring chamber and a measuring sensor. However, the use of a measuring chamber with a vapor deposition is particularly advantageous. It is particularly advantageous to construct the measuring chamber such that a part of the emitted light that is as large as possible is directed to the measuring sensor. The measuring chamber has, for example, an essentially elliptic cross-section, in which case the fiber-optical waveguide is installed in one focal line, and the sensor is installed on the second focal line. If desired, the light yield may be optimized by the use of a focus adapter. A person skilled in the art will easily be able to optimally adapt the shape of the measuring chamber to the geometry of the fiber-optical waveguide and of the sensor.

In a further preferred embodiment, the sensor encloses the fiber-optical waveguide in the shape of a cylinder.

The fluorescence signal is measured in a time-staggered manner with respect to the light excitation. As a result, it is possible to adapt the measuring of the fluorescence light to the time sequence of the fluorescence/phosphorescence process. In addition, it is possible, when several fluorophores with varying die-away characteristics are used, to discriminate between them. For the time-resolved detection, either so-called boxcar photomultiplier combinations or diode arrays can be used, or a so-called phase-resolving detector system (E. Gaviola, Z. Phys., 42 [1927] 853-61; L. McGown, Anal. Chem. 56 [1984] 1400-15) is used. As a result, an additional measuring parameter can be utilized in addition to the optical wavelength. It is therefore possible to determine by means of a suitable fluorophore selection, in one measuring fiber-optical waveguide, many elements to be analyzed in one measuring process. On the basis of the analytical data, by way of a data processing system, diagnoses can then be made or the further procedure can be determined.

The other constructional characteristics, such as the monochromator, the optical filters, the sensors, etc. correspond to those of conventional fluorometers.

In the following, the invention is explained in detail by means of FIGS. 1 to 4.

Figure 1:
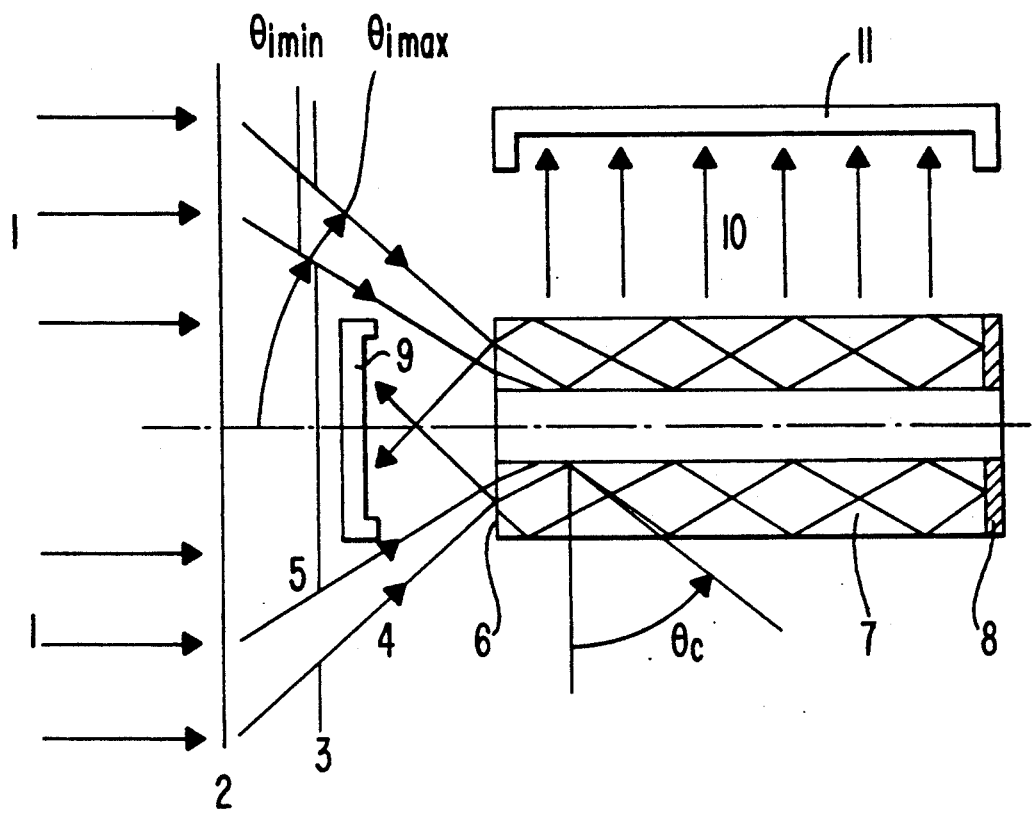
FIG. 1 is a schematic longitudinal sectional view of a measuring arrangement.

In FIG. 1, the light 1 impinges on a focussing lens represented by the lens plane 2 through an aperture which is provided with a ring-shaped aperture opening. As a result, a conical-envelope-shaped guiding of the light is obtained. The conical shell is represented by the outer boundary beam 4 and the inner boundary beam 5. The light enters into the measuring fiber-optical waveguide 7 at the front face 6. The further optical path through the measuring fiber-optical waveguide by multiple total reflection is indicated schematically. On the end of the measuring fiber-optical waveguide 7, which is opposite the beaming-in of the light, by means of a mirror 8, the light can pass through the measuring optical waveguide 7 in the reverse direction. After its emergence, a portion of the light can then be sensed by an auxiliary sensor 9. On the lumen surface of the measuring fiber-optical waveguide, substances capable of fluorescence can radiate light by the total reflection of the excitation radiation. The emitted fluorescence radiation 10 may be detected by the measuring sensor 11. By means of optoelectronic devices, such as a boxcar 19 (FIG. 4), the emitted light can be measured as a function of time with respect to the excitation. $\Theta_{i\ min}$ and $\Theta_{i\ max}$ are the minimal and maximal angles of incidence of the excitation radiation, while $\Theta_c$ indicates the critical angle for the total reflection in the interior of the fiber-optical waveguide.

Figure 2:
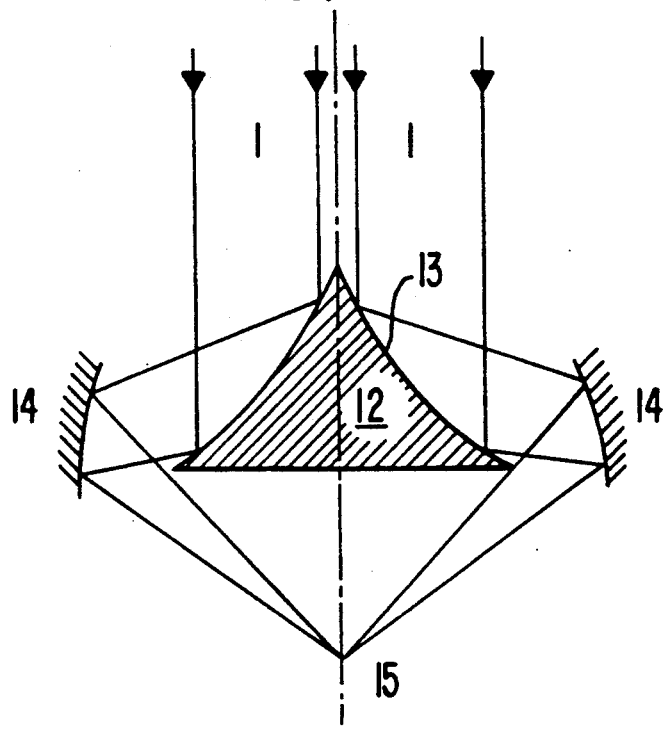
FIG. 2 is a schematic longitudinal sectional view of a mirror combination for generating a conical-envelope-shaped guiding of the light.

FIG. 2 illustrates how the light 1 impinges on the central mirror 12 and is guided by its spheroidal mirror surfaces 13 by way of the ring-shaped outer mirror 14, to the focal point 15. Both mirrors are rotationally symmetrical and have a common axis of symmetry.

Figure 3A:
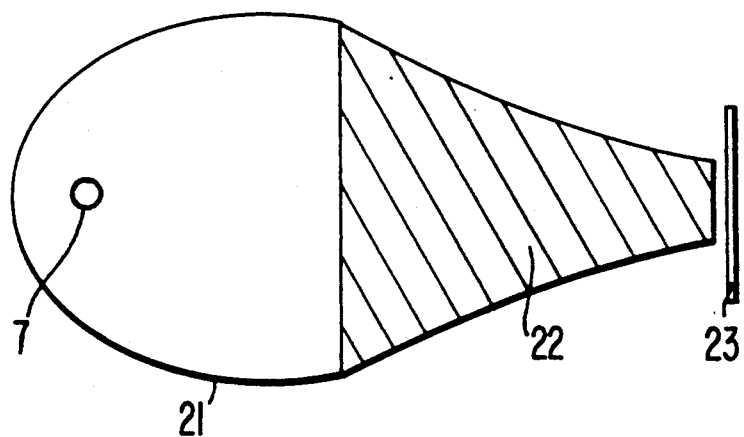
FIGS. 3a and 3b are schematic views of two cutting planes through a measuring chamber arrangement which are disposed perpendicularly with respect to one another.
Figure 3B:
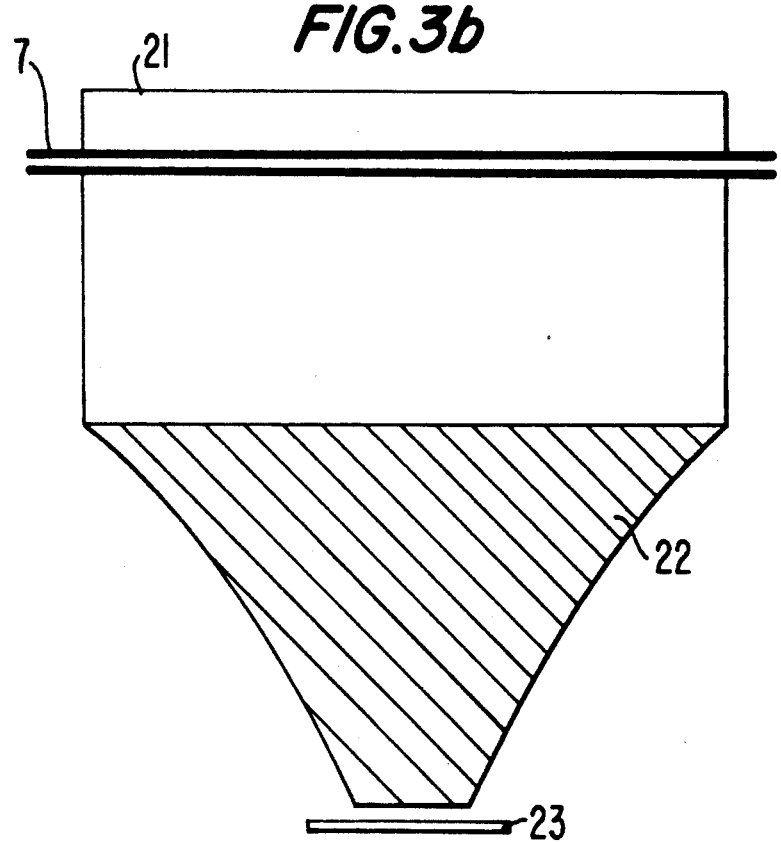

FIG. 3 schematically illustrates an example of a measuring chamber arrangement by means of two cutting planes which are disposed perpendicularly with respect to one another. The measuring fiber-optical waveguide 7 is situated on the focal line of a paraboloidal or ellipsoidal reflector 21 with a mirror. A focus adapter 22 is connected to the reflector 21. This focus adapter 22 focusses the light emerging from the reflector 21 on the schematically illustrated entrance lens system 23 of a monochromator or of a filter arrangement. The optimization of the design of the reflector 21 and of the focus adapter 22 as well as their mutual arrangement takes place according to calculating rules which are known per se.

Figure 4:
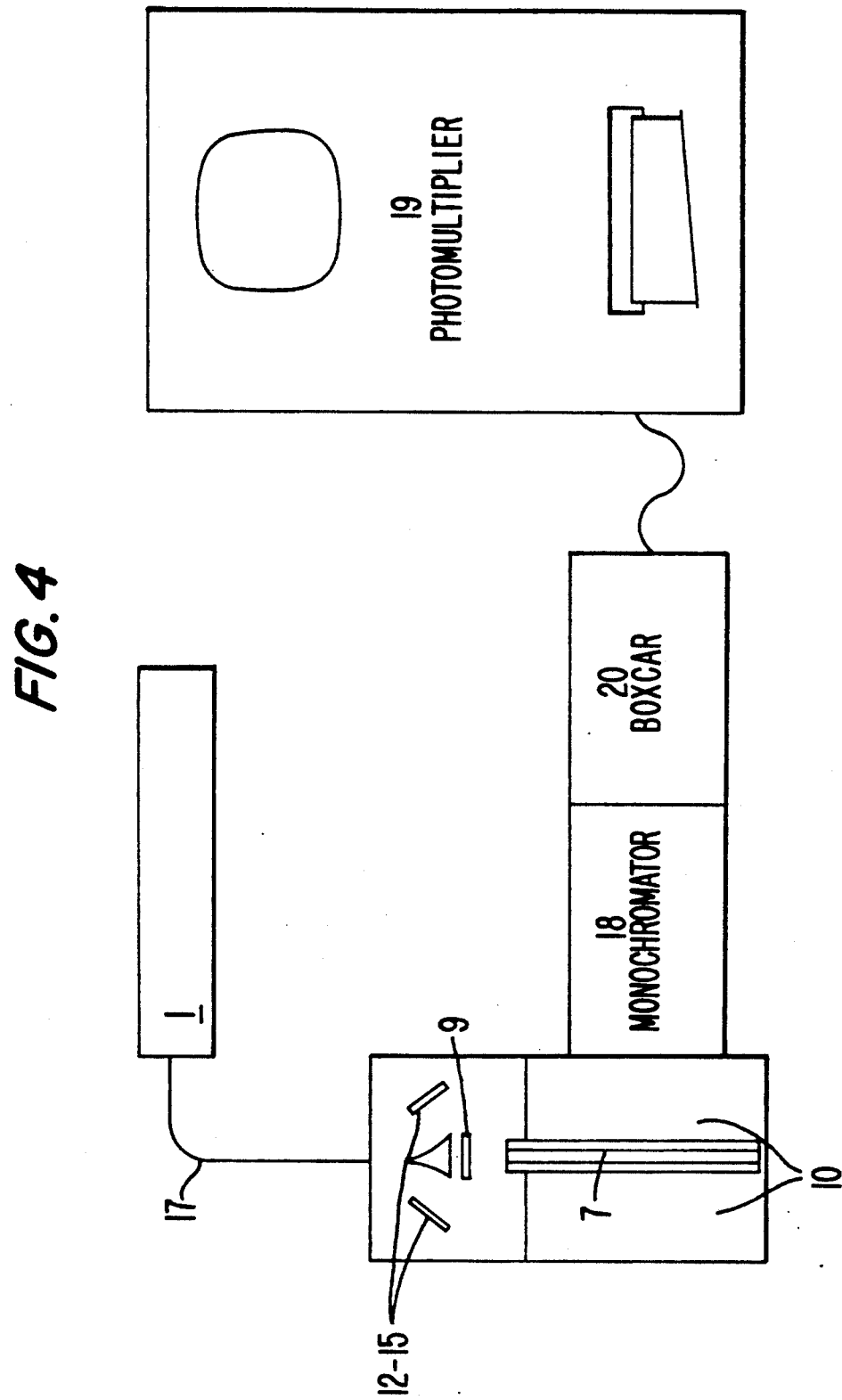
FIG. 4 is a schematic view of a preferably claimed construction of a measuring arrangement.

FIG. 4 schematically illustrates a measuring device which brings the laser light 1 by way of fiber-optical waveguide 17 to the entrance lens system 12 to 15 into the measuring fiber-optical waveguide 7 and, by means of the auxiliary sensor 9, carries out controlling and correcting measurements. Fluorescence radiation 10 of the substances to be measured quantitatively is guided by way of a monochromator (or filter system) 18 to the photomultiplier 20 with the connected boxcar 19.

What is claimed:

1. A reflection fluorometer, comprising:
   a capillary-shaped measuring fiber-optical waveguide;
   means for providing a conical envelope shaped beam of pulsed light onto a front face of the measuring optical waveguide; and
   a device for the time-resolved measurement of emission light which emerges in a substantially radial manner from the measuring optical waveguide.

2. A reflection fluorometer according to claim 1, further comprising a device for wavelength-resolved measurement of emission light which emerges in a substantially radially manner from the measuring fiber-optical waveguide.

3. A device according to claim 1, wherein the measuring optical waveguide has a mirror on the end opposite the beam of light.

4. A reflection fluorometer according to claim 1, further comprising an auxiliary sensor for measuring a portion of reflected light or of emission light for the compensation and correction of the measured values.

5. A reflection fluorometer according to claim 1, wherein the measuring fiber-optical waveguide is situated on a focal line of a reflector which has an elliptic or paraboloidal cross-section.

6. A reflection fluorometer, according to claim 5, wherein a focus adaptor is connected to the reflector along the focal line of the reflector.

7. A reflection fluorometer according to claim 2, wherein the measuring fiber-optical waveguide has a vapor deposition on the end opposite the beaming-in of the light.

8. A reflection fluorometer according to claim 2, further comprising an auxiliary sensor for measuring a portion of reflected light or of the emission light for the compensation and correction of the measured values.

9. A reflection fluorometer according to claim 2, wherein the measuring fiber-optical waveguide is situated on a focal line of a reflector which has an elliptic or paraboloidal cross-section.

* * * * *